United States Patent
Han et al.

(10) Patent No.: US 11,096,617 B2
(45) Date of Patent: Aug. 24, 2021

(54) SYSTEM AND METHOD FOR DETECTING ASSOCIATED CARDIAC ACTIVATIONS

(71) Applicant: ST. JUDE MEDICAL, CARDIOLOGY DIVISION, INC., St. Paul, MN (US)

(72) Inventors: Dongfeng Han, St. Paul, MN (US); Valtino X. Afonso, Oakdale, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 132 days.

(21) Appl. No.: 16/482,685

(22) PCT Filed: Jan. 25, 2018

(86) PCT No.: PCT/US2018/015224
§ 371 (c)(1),
(2) Date: Jul. 31, 2019

(87) PCT Pub. No.: WO2018/148023
PCT Pub. Date: Aug. 16, 2018

(65) Prior Publication Data
US 2020/0237245 A1 Jul. 30, 2020

Related U.S. Application Data

(60) Provisional application No. 62/457,024, filed on Feb. 9, 2017.

(51) Int. Cl.
*A61B 5/287* (2021.01)
*A61B 5/339* (2021.01)
(Continued)

(52) U.S. Cl.
CPC .............. *A61B 5/349* (2021.01); *A61B 5/287* (2021.01); *A61B 5/339* (2021.01); *A61B 5/341* (2021.01); *A61B 5/333* (2021.01)

(58) Field of Classification Search
None
See application file for complete search history.

(56) References Cited

U.S. PATENT DOCUMENTS

2015/0374261 A1\* 12/2015 Grunwald .............. A61B 5/316
600/381

OTHER PUBLICATIONS

International Search Report and Written Opinion for International Application No. PCT/US2018/015224, dated Apr. 4, 2018, 11 pages.

(Continued)

*Primary Examiner* — Brian T Gedeon
(74) *Attorney, Agent, or Firm* — Armstrong Teasdale LLP (57) ABSTRACT

The present disclosure provides systems and methods for detecting cardiac activation times of a patient. A system includes a data acquisition system and a processor communicatively coupled thereto. The data acquisition system is configured to detect a plurality of electrograms generated at a plurality of respective electrodes coupled to the patient. The processor is configured to receive the plurality of electrograms from the data acquisition system. The processor is further configured to compute respective energies of the plurality of electrograms. The processor is further configured to detect a cardiac activation time for a first electrogram among the plurality of electrograms based on the respective energy of the first electrogram and the respective energy of a second electrogram that neighbors the first electrogram.

20 Claims, 10 Drawing Sheets

(51) Int. Cl.
    *A61B 5/349*    (2021.01)
    *A61B 5/341*    (2021.01)
    *A61B 5/333*    (2021.01)

(56) References Cited

OTHER PUBLICATIONS

M.P. Nguyen et al.: "A new approach for automated location of active segments in intracardiac electrograms" In: "IFMBE proceedings (International Federation for Medical and Biological Engineering)", 25/4, Sep. 7, 2009, Springer, DE, pp. 763-766.

C.D. Cantwell et al: "Techniques for automated local activation time annotation and conduction velocity estimation in cardiac mapping", Computers in Biology and Medicine, 65, Apr. 25, 2015, pp. 229-242.

Jack M. Rogers et al.: "A quantitative framework for analyzing epicardial activation patterns during ventricular fibrillation", Annals of Biomedical Engineering, 25/5, Sep. 1, 1997, pp. 749-760.

Liqian Sun et al.: "A preliminary study on atrial epicardial mapping signals based on Graph Theory", Medical Engineering & Physics., 36/7, Jul. 1, 2014, pp. 875-881.

* cited by examiner

SYSTEM AND METHOD FOR DETECTING ASSOCIATED CARDIAC ACTIVATIONS

CROSS REFERENCE TO RELATED APPLICATIONS

This application is the national stage entry of PCT/US2018/015224, filed on Jan. 25, 2018, which claims the benefit of priority to U.S. provisional application Ser. No. 62/457,024, filed Feb. 9, 2017, which are incorporated herein by reference in their entirety.

A. FIELD OF THE DISCLOSURE

The present disclosure relates generally to electrocardiography. In particular, in many embodiments, the present disclosure relates to systems and methods for detecting cardiac activations.

B. BACKGROUND OF THE DISCLOSURE

It is generally known, in physiology, that cells undergo periodic depolarization and repolarization that is essential to the functioning of and communication among those cells. Depolarization is a process by which a cell at resting potential, which is generally a negative internal charge and a relatively positive membrane charge, shifts such that the internal charge becomes more positive. Conversely, repolarization is a complimentary process by which the cell's charge shifts back toward resting potential.

During a cardiac cycle, cells of the atria first depolarize, causing contraction. The depolarization propagates over time, like a wave, arriving at cells of the ventricles as the atria finish contracting. Depolarization in the ventricles causes contraction, while the atria are repolarized and relaxed. The ventricles then repolarize and relax.

Electrocardiography is a technology by which cardiac electrical activity is monitored and recorded over time. Generally, the depolarization and repolarization patterns of the heart are detectable as small changes in charge in skin cells that are measured using, for example, various cutaneous electrodes. A graph of these charges, i.e., voltages, is referred to as an electrocardiogram (ECG). A typical ECG utilizes ten cutaneous electrodes placed in various locations on the limbs and chest. ECGs are often used to measure rate and rhythm of heartbeats, as well as to evaluate the cardiac cells to detect damage or diagnose potential heart conditions.

Additionally, in electrophysiological procedures, an array of electrodes located on a distal end of a cardiac catheter is placed on the cardiac muscle to produce an electrogram. Cardiac catheter electrodes generally include, for example, and without limitation, unipole and bipole electrodes. Bipole electrodes are self-referencing, measuring a potential across two contacts. Unipole electrodes are referenced to a common potential.

Each electrode of the ECG and electrogram produces ECG and electrogram traces. A fundamental aspect of the ECG and electrogram is the accurate detection of cardiac activations in each trace. Such detections are an ongoing challenge in creating useful products from an ECG and electrogram, including, for example, and without limitation, a local activation time (LAT) map, a regular cycle length map, a voltage map, and a conduction velocity map.

BRIEF SUMMARY OF THE DISCLOSURE

The present disclosure generally relates to electrocardiography and systems and methods for detecting cardiac activations. In many embodiments, the systems include an electrocardiogram system that provides accurate detection of cardiac activation times for producing the electrical activity maps. Embodiments of the systems and methods described herein utilize a neighborhood of electrograms for detecting an activation time in each electrogram. Such a neighborhood may include bipole and unipole electrograms, and a surface electrocardiogram (ECG). Systems and methods described herein further utilize spatial and time constraints on the neighborhood to carry out the cardiac activation time detection. Systems and methods described herein utilize criteria for the electrograms to mitigate the effects of far field cardiac electrical activity.

In one embodiment, the present disclosure provides a system for detecting cardiac activation times of a patient. The system includes a data acquisition system and a processor communicatively coupled thereto. The data acquisition system is configured to detect a plurality of electrograms generated at a plurality of respective electrodes coupled to the patient. The processor is configured to receive the plurality of electrograms from the data acquisition system. The processor is further configured to compute respective energies of the plurality of electrograms. The processor is further configured to detect a cardiac activation time for a first electrogram among the plurality of electrograms based on the respective energy of the first electrogram and the respective energy of a second electrogram that neighbors the first electrogram.

In another embodiment, the present disclosure is directed to method of detecting cardiac activation times for a patient's heart. The method includes receiving a plurality of electrograms; computing respective energies of the plurality of electrograms; constructing a graph representing the plurality of electrograms based on the respective energies and respective neighboring electrograms of the plurality of electrograms; and employing a maximum flow solution on the graph to determine respective cardiac activation times for the plurality of electrograms.

In another embodiment, the present disclosure is directed to a method of conducting an electrocardiogram (ECG) on a patient. The method includes measuring cardiac electrical activity using a plurality of surface electrograms; computing a representative surface electrogram based on the plurality of surface electrograms; measuring the cardiac electrical activity using a cardiac catheter having a plurality of catheter electrodes arranged in a grid that produce a neighborhood of electrograms; computing respective energies for the neighborhood of electrograms; constructing an s-t graph for the neighborhood of electrograms and representing a maximum flow problem; and computing a solution to the maximum flow problem to determine a cardiac activation time for each electrogram of the neighborhood of electrograms.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

The present disclosure relates generally to electrocardiography. In particular, in many embodiments, the present disclosure relates to systems and methods for detecting cardiac activations for use in producing electrical activity maps. Such maps are generally produced from bipole electrograms that are dependent on direction of the cardiac wave-front relative to an orientation of the bipole electrode pair. It is further realized herein that such electrograms may include artifacts introduced by far-field cardiac electrical activity. For example, a unipole or bipole electrogram measured in the atria may have deflections due to cardiac activity occurring concurrently in the ventricles.

Embodiments of the systems and methods described herein provide an electrocardiogram system that provides accurate detection of cardiac activation times for producing the electrical activity maps. Embodiments of the systems and methods described herein utilize a neighborhood of electrograms for detecting an activation time in each electrogram. Such a neighborhood may include bipole and unipole electrograms, and a surface electrocardiogram (ECG). Systems and methods described herein further utilize spatial and time constraints on the neighborhood to carry out the cardiac activation time detection and also utilize criteria for the electrograms to mitigate the effects of far field cardiac electrical activity.

Figure 1:
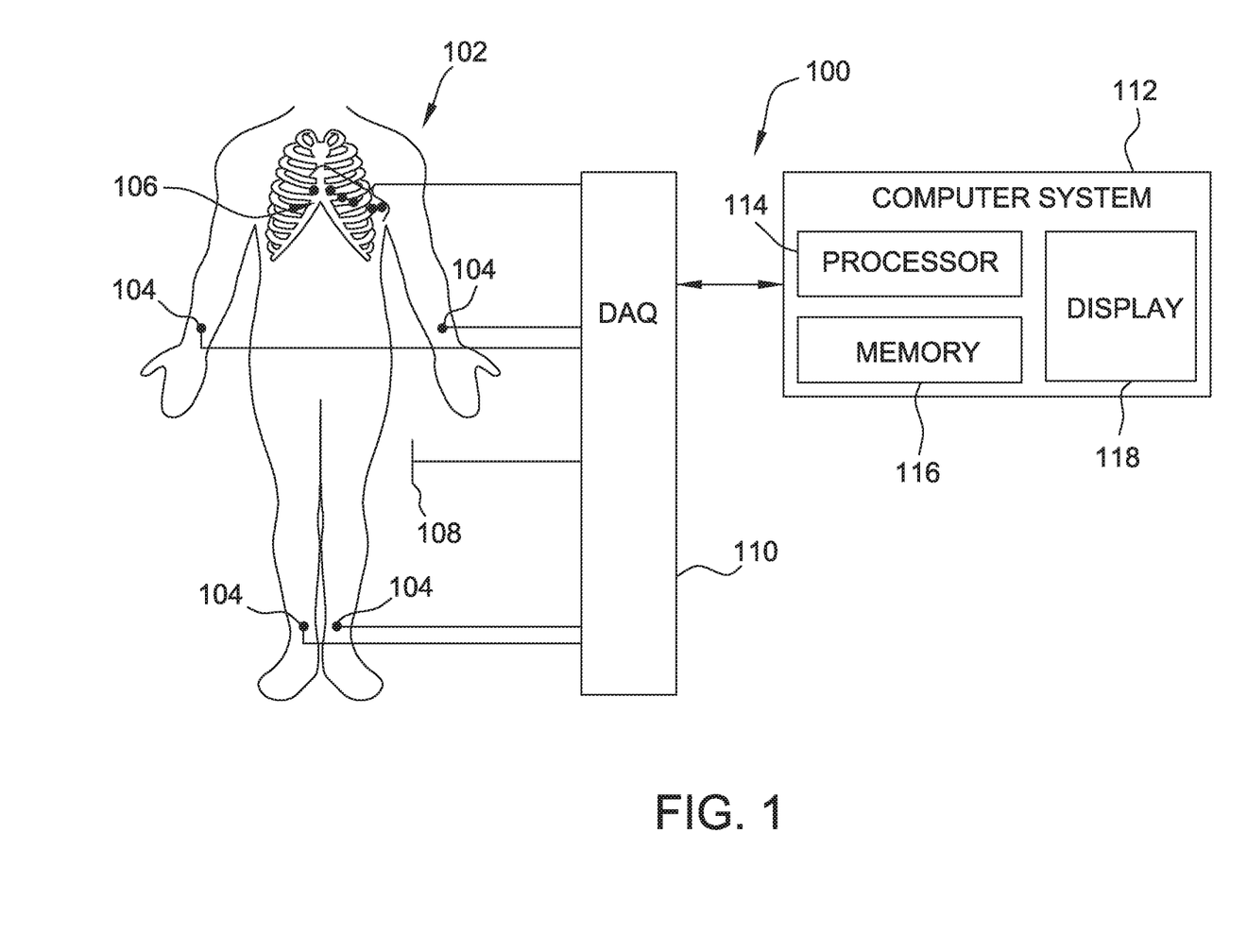
FIG. 1 is a schematic diagram of a system for conducting an electrocardiogram.

FIG. 1 is a schematic and block diagram of an ECG system 100 for conducting an ECG on a patient 102. ECG System 100 shown in FIG. 1 is sometimes referred to as a surface ECG that measures electrical activity of patient 102's heart using various cutaneous electrodes, including limb electrodes 104 and precordial electrodes 106. System 100, in certain embodiments may further include internal electrodes (not shown) inserted into patient 102 using a cardiac catheter. System 100 includes a common electrode 108 that, in certain embodiments, serves as a common reference for others of limb electrodes 104 and precordial electrodes 106, and, more specifically, any unipole electrodes among them.

Figure 2:
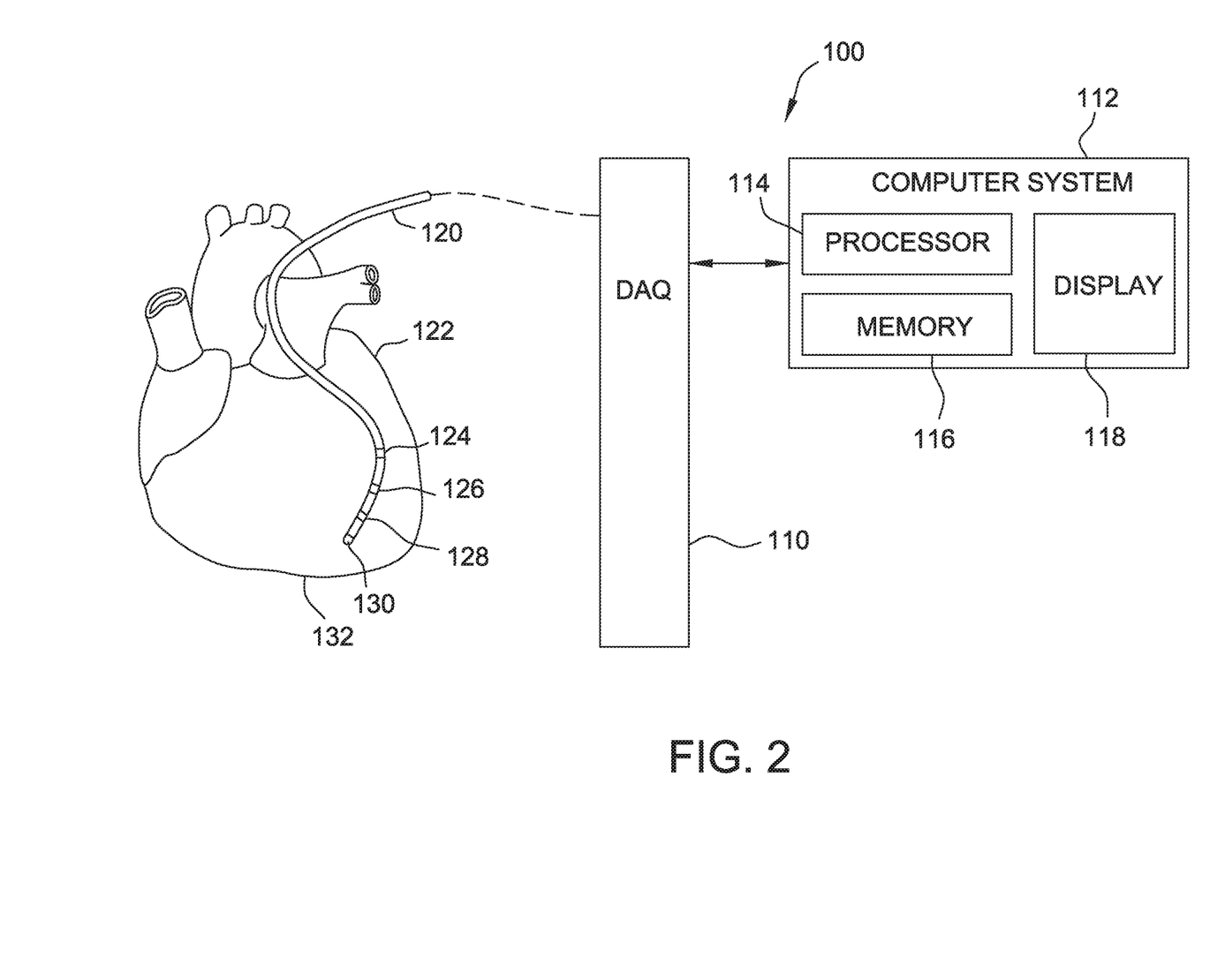
FIG. 2 is a schematic diagram of the system of FIG. 1 having a catheter.

FIG. 2 is another schematic and block diagram of ECG system 100, including a catheter 120 having various catheter electrodes 124, 126, 128, and 130, sometimes referred to as distal electrodes. Catheter 120, in certain embodiments, may utilize a single catheter having numerous splines, each with multiple electrodes. In alternative embodiments, system 100 may utilize multiple catheters 120, each with multiple electrodes. In certain embodiments, catheter 120 is embodied in a high-density grid catheter, such as the EnSite™ Array™ non-contact mapping catheter of St. Jude Medical, Inc. Catheter 120 is generally introduced to heart 122, vasculature, or ventricle 132 of patient 102 utilizing one or more introducers and using known procedures. Catheter 120 includes bipole electrodes and unipole electrodes.

FIG. 3A is a schematic diagram of an exemplary catheter system 300. Catheter system 300 includes a handle 302 and connectors 304 disposed proximal to handle 302 for making electrical connections to an electronic mapping system or other suitable computing system. Catheter system 300 includes an introducer sheath 306 located distal to handle 302 that a surgeon may use to deliver a sheath 308 into the body of patient 102. Sheath 308 extends from introducer sheath 306. Catheter system 300 further includes an electrode assembly 310 that protrudes from the distal end of sheath 308. Catheter system 300 may be embodied, for example, and without limitation, in catheter systems described in U.S. Pat. No. 8,224,416, assigned to St. Jude Medical Inc., which is hereby incorporated by reference herein.

FIG. 3B is a schematic diagram of an exemplary electrode assembly 310, for use in catheter system 300. Electrode assembly 310 includes a catheter body 312 coupled to a paddle 314. Catheter body 312 includes a first body electrode 316 and a second body electrode 318. Paddle 314 includes a first spline 320, a second spline 322, a third spline 324, and a fourth spline 326 coupled to catheter body 312 by a proximal coupler 328 and coupled to each other by a distal connector 330 at a distal end 332 of paddle 314. In one embodiment, first spline 320 and fourth spline 326 are one continuous segment and second spline 322 and third spline 324 are another continuous segment. In alternative embodiments, each of splines 320, 322, 324, and 326 are separate segments coupled to each other. Splines 320, 322, 324, and 326 include electrodes 334. Electrodes 334 may be embodied, for example, in ring electrodes evenly spaced along splines 320, 322, 324, and 326. In alternative embodiments, electrodes 334 may be embodied in point electrodes or any other suitable type of electrode.

Electrical activity produced by the heart manifests as small changes in charge of various cells of patient 102 that are detectable using specialized instrumentation, such as a data acquisition system (DAQ) 110 that is connected to surface ECG electrodes and the various electrodes of catheter 120. DAQ 110 includes various analog and digital circuits for sensing, conditioning, and relaying the electrogram signals generated at limb electrodes 104, precordial electrodes 106, and catheter electrodes to a computing system 112.

Computing system 112 includes a processor 114, a memory 116, and a display 118. Computing system 112 may be embodied by the EnSite NavX™ system of St. Jude Medical, Inc., which is capable of measuring electrical activity of patient 102's heart to generate electrical activity maps that are produced using the apparatus and methods described herein. Such electrical activity maps, in certain embodiments, may not be generated within computing system 112. Computing system 112 may further be embodied by other ECG systems, such as, for example, the CARTO system of Biosense Webster, Inc., or the AURORA® system of Northern Digital Inc.

Computing system 112 is configured to receive multiple electrograms from DAQ 110 and present them on display 118 for viewing by a user, such as, for example, a physician, clinician, technician, or other user. Computing system 112 may further be configured to record the multiple electrograms in memory 116. Processor 114 is configured to process the multiple electrograms to determine an activation time for a given cardiac cycle. Such activation times are fundamental to producing electrical activity maps, such as the local activation time (LAT) map, the regular cycle length map, the voltage map, and the conduction velocity map.

Figure 4:
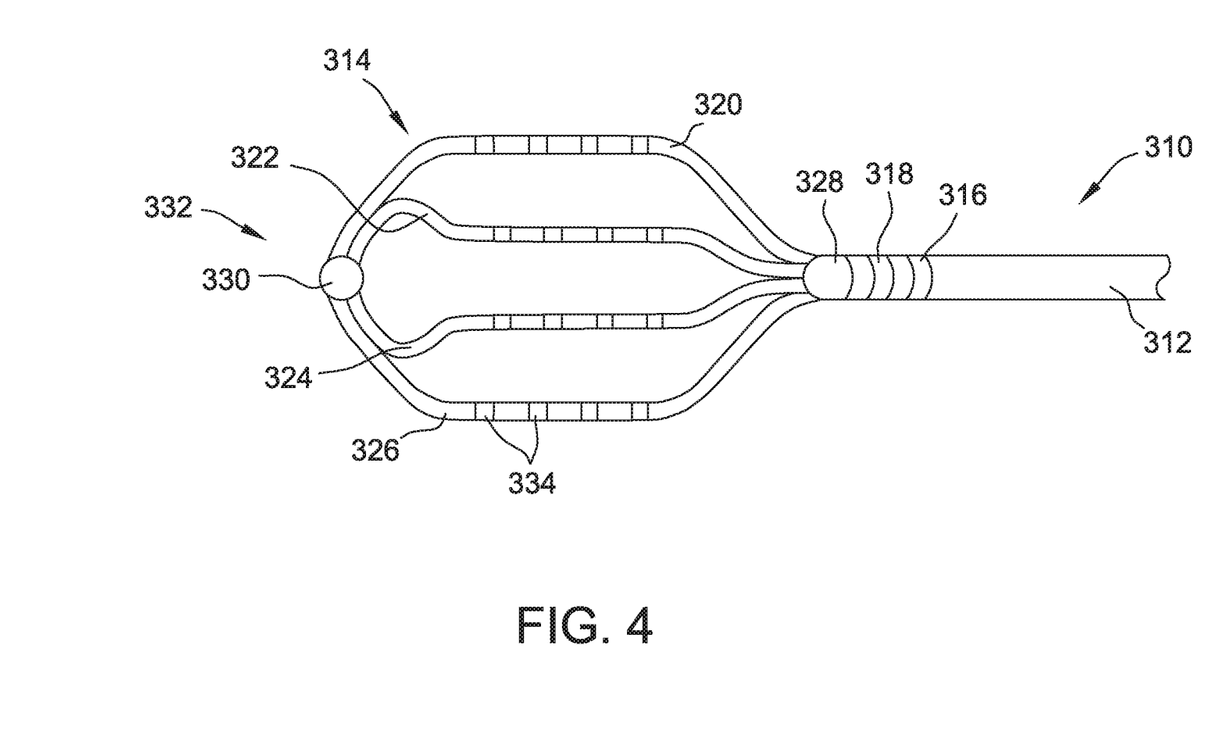
FIG. 4A is an illustration of an exemplary set of electrograms.
FIG. 4B is another illustration of the exemplary set of electrograms shown in FIG. 4A.
Figure 4A:
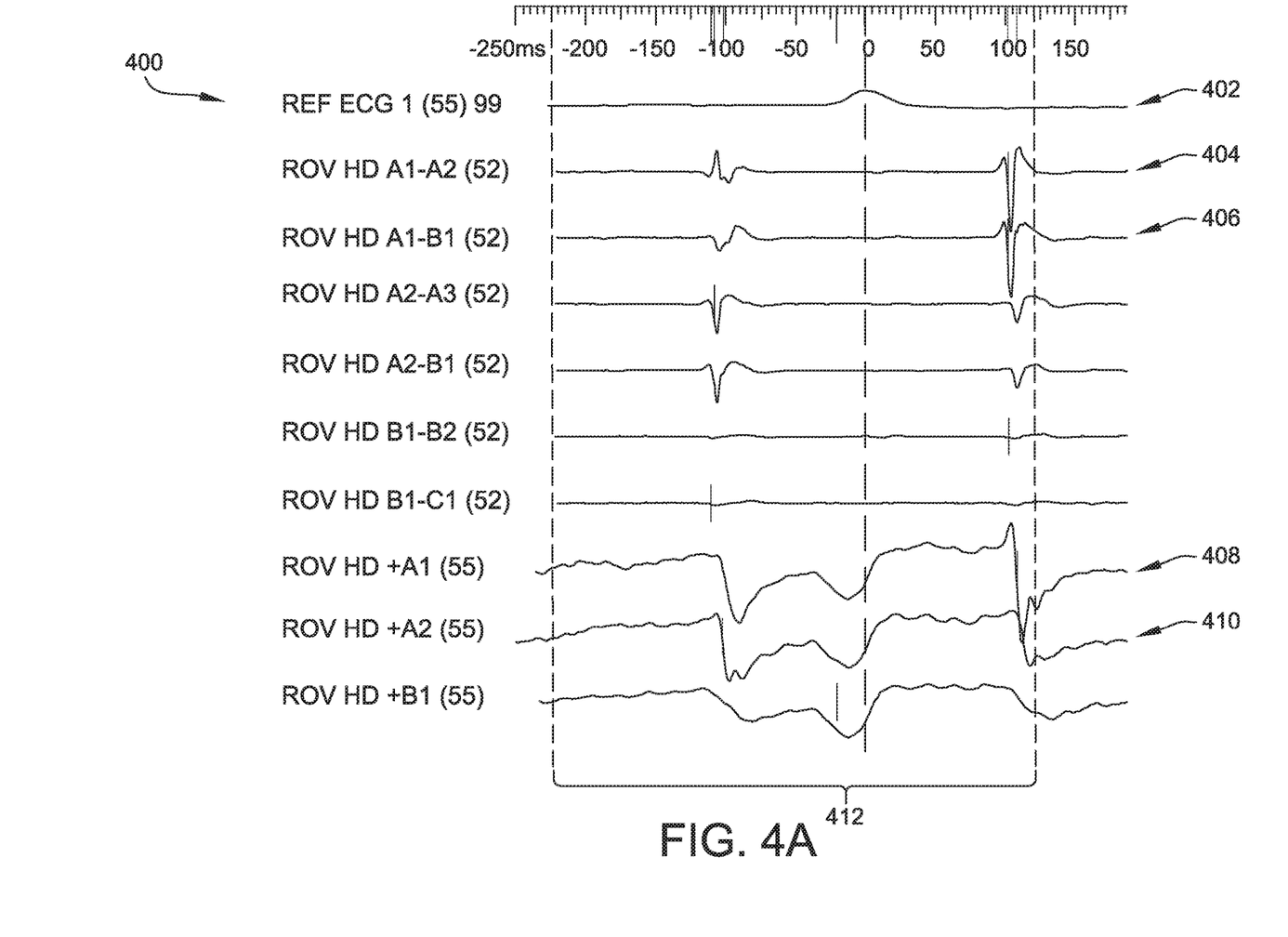

FIG. 4A is an illustration of an exemplary set of electrograms 400 generated by various unipole and bipole electrodes of the surface ECG and catheter 120 displayed on a computing system, such as, for example, computing system 112. The set of electrograms shown in FIG. 4 include a reference ECG 402 produced by the surface ECG, and multiple electrograms produced by multiple catheter electrodes placed in the heart of the patient. The electrograms include, for example, electrograms 404 and 406 corresponding to bipole electrodes. The electrograms further include, for example, electrograms 408 and 410 corresponding to unipole electrodes.

Figure 4B:
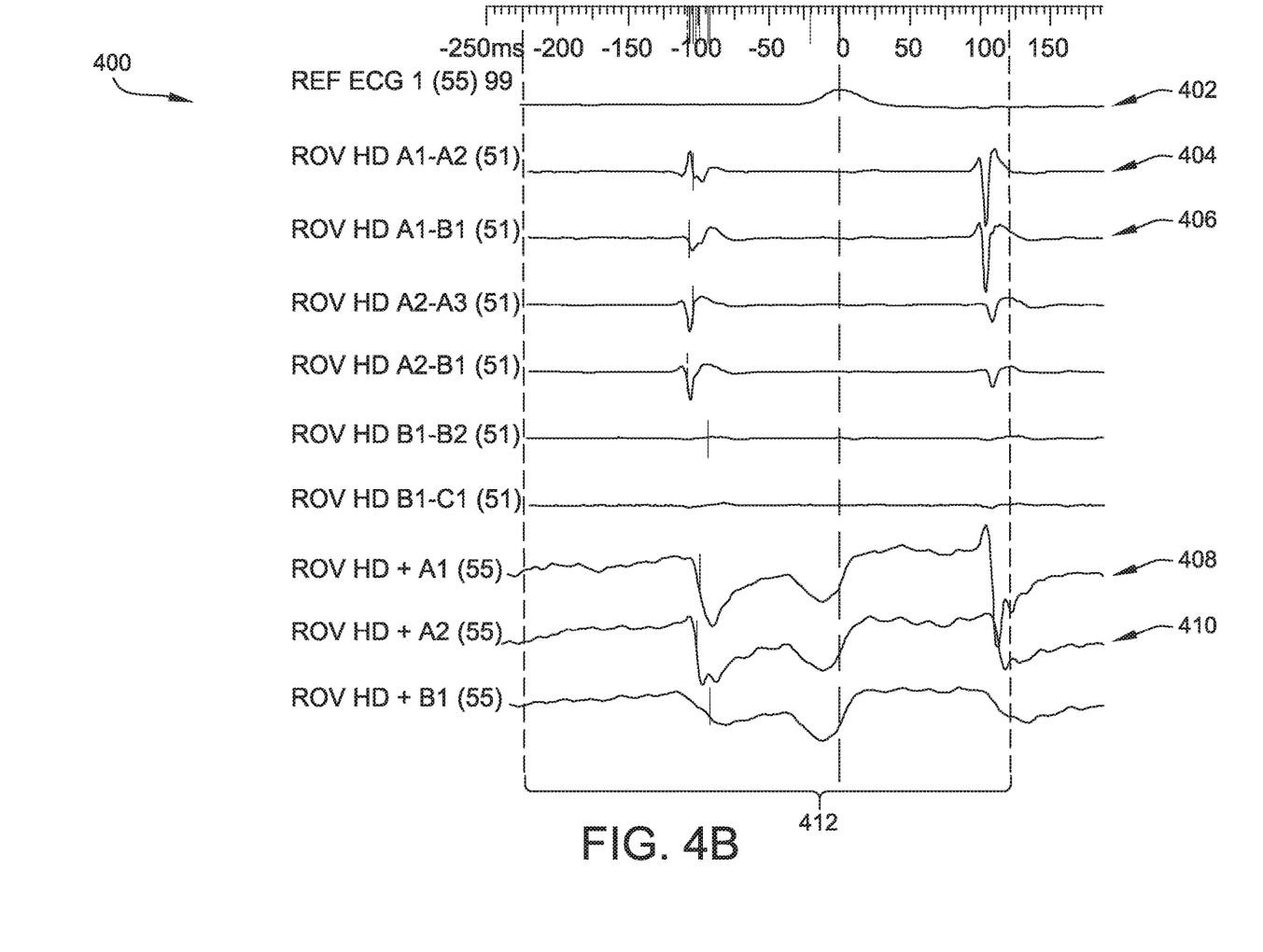

FIG. 4B is another illustration of the exemplary set of electrograms 400 generated by the various unipole and bipole electrodes of the surface ECG and catheter 120. FIG. 4B again illustrates reference ECG 402 produced by the surface ECG, and multiple electrograms produced by catheter electrodes, including, for example, electrograms 404 and 406 corresponding to bipole electrodes, and electrograms 408 and 410 corresponding to unipole electrodes.

A typical electrical activity map is generated by a user having selected a cardiac signal to use as a reference signal, and a time window of interest (WOI), sometimes referred to as a curtain. Generally, the user selects a WOI long enough in duration to contain a single cardiac activation. Processor 114 processes the electrograms to compute an activation response and then selects a time of the largest response as the activation time. Generation of such a map is sensitive to the user input, particularly the selection of a correct WOI that envelopes a single cardiac activation. Consequently, a given WOI often contains multiple activations, among which processor 114 cannot properly distinguish for generating the electrical activity map. For example, in generating a LAT map from a set of electrograms illustrated in FIG. 4A, two neighboring electrograms may have activation times from different cardiac cycles, resulting in a large and incorrect difference in the LAT map.

FIG. 4A and FIG. 4B illustrate a WOI 412 within which, for certain electrograms, multiple cardiac activations occur. The user-selected WOI is generally in the range of 100 milliseconds to 500 milliseconds. For example, a user may select a WOI that is 300 milliseconds in duration. FIG. 4A further illustrates the disparate detected activations among the set of electrograms, indicated by the vertical yellow markers located on each trace. FIG. 4B further illustrates detected activations using the systems and methods described herein.

In embodiments of system 100 and methods described herein, processor 114 considers a neighborhood of electrograms and far-field electrical activity in detecting an activation time for each electrogram. A neighborhood of electrograms is two or more electrograms produced from electrodes that are spatially proximate each other. By considering a neighborhood of electrograms, embodiments of system 100 and methods described herein, for a given electrogram i, utilize surrounding electrogram signals, including surface ECG, to aid in the detection of local cardiac activations. In considering a neighborhood of electrograms, embodiments of the systems and methods described herein are enabled to enforce spatial and time constraints on detecting cardiac activations to ensure two nearby electrograms have cardiac activation times within a specified time of each other.

In detecting a cardiac activation time for a given electrogram, i, processor 114 processes the electrogram response within the following framework that arranges the problem as an energy minimization problem, where the energy, w, of a given electrogram over time, i.e., w(t), is the inverse of that electrogram's response. A total energy, E, is then computed as the sum of energies of each electrogram at its detected local activation time, t, which exists in a set, T, of time samples. The size of set T may change for various computations. Further, a function, s, is defined to determine the local activation time for a given electrogram, is s(i)=t.

$$E = \sum_{i=1}^{M} w(s(i)) + \Sigma_{(i,j) \in N} h(s(i), s(j)) \qquad \text{EQ. 1}$$

$$h(s(i), s(j)) = \begin{cases} +\infty & \text{if } |s(i) - s(j)| \geq \Delta \\ 0, & \text{else} \end{cases} \qquad \text{EQ. 2}$$

where, M is the number of electrograms, j denotes an electrogram within a neighborhood N within which a given electrogram, i, resides, h is a system for neighborhood N, Δ is a local activation time difference constraint for system h. Processor 114 processes the electrograms according to the above framework to determine an s that minimizes total energy, E, defined in EQ. 1.

Figure 5:
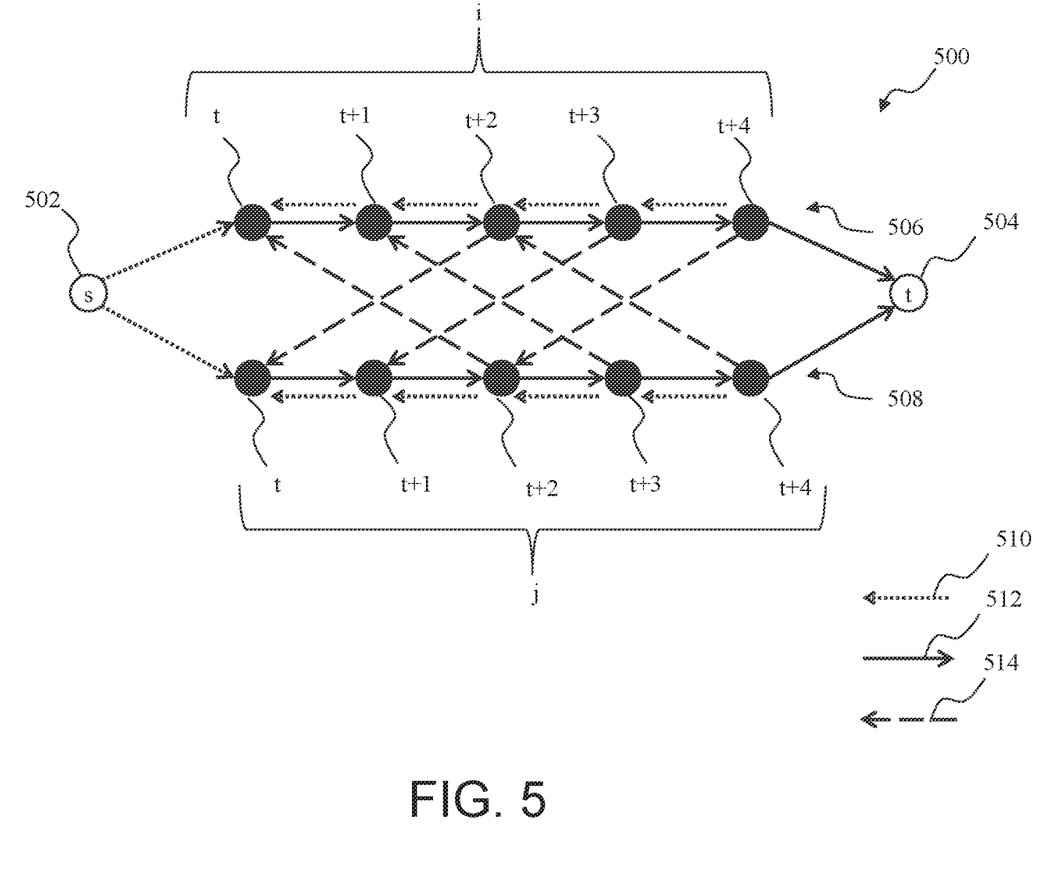
FIG. 5 is an exemplary graph illustrating relationships between a given electrogram and a neighboring electrogram.

Embodiments of system 100 and methods described herein utilize graph theory to minimize the total energy, E, defined in EQ. 1. For example processor 114 discretizes a given electrogram, i, into samples indexed by t. Processor 114 then constructs a graph for electrogram i composed of one node per sample, as illustrated in FIG. 5. FIG. 5 is an exemplary graph 500 illustrating pair-wise relationships among two electrograms. Graph 500 is a weighted directed graph that represents the relationship between electrogram i and a neighboring electrogram, j, and as such, graph 500 also includes one node per sample of electrogram j, also indexed by t.

Graph 500 is constructed as a maximum flow problem, where the maximum flow from a single source 502, denoted as "s," to a single sink 504, denoted as "t," passes through a network of nodes 506 for electrogram i and nodes 508 for electrogram j. Graph 500 further includes edges 510, 512, and 514 that quantify the "flow" among the nodes. The maximum flow problem has a solution that states the maximum flow from source 502 to sink 504 is defined by a "minimum cut" that severs source 502 from sink 504. The value of a cut is determined by the values, or weights, assigned to edges 510, 512, and 514. By identifying the minimum cut in graph 500, processor 114 minimizes the total energy, E, defined in EQ. 1. In the embodiments of system 100 and methods described herein, the maximum flow problem is solved simultaneously for all electrograms. The maximum flow problem is solvable using known methods, including, for example, and without limitation, the methods described in Ford, Lester R., and Delbert R. Fulkerson, "Maximal Flow Through a Network," Canadian Journal of Mathematics 8.3 (1956), pages 399-404, in Cormen, Thomas H., "Introduction to Algorithms," MIT Press, 2009, in Boykov, Yuri, Olga Veksler, and Ramin Zabih, "Fast Approximate Energy Minimization via Graph Cuts," Pattern Analysis and Machine Intelligence, IEEE Transactions on 23.11 (2001), pages 1222-1239, an in Ishikawa, Hiroshi, "Exact Optimization for Markov Random Fields with Convex Priors," Pattern Analysis and Machine Intelligence, IEEE Transactions on 25.10 (2003), pages 1333-1336, all of which are hereby incorporated by reference herein.

In certain embodiments, for mapping irregular cardiac rhythms, a refractory parameter is set and graph 500 is split into the left and right portions with respect to the "minimum cut." The solution to the maximum flow problem is then recursively applied, reconstructing graph 500 from the remaining nodes, such that another cardiac activation time is detected. The refractory parameter represents a refractory period for cardiac muscle cells as they return to a resting state after a cycle of depolarization and repolarization, i.e., a cardiac activation. Generally, the cardiac muscle cells cannot respond to stimuli to initiate another action potential because the channels that initiate depolarization are inactive until the cells are repolarized or hyperpolarized. The refractory period corresponds to a representative cycle length for the irregular rhythm. For example, for atrial fibrillation, the refractory parameter may be user specified or automatically determined based on a coronary sinus catheter, a left atrial catheter, or a right atrial catheter. The refractory period is typically between about 40 and 300 milliseconds and varies under certain circumstances.

For graph 500, processor 114 computes edges 510, 512, and 514. Edges 510 are drawn between samples of electrogram i and between samples of electrogram j, and are assigned a weight of positive infinite to ensure a single node is detected. Edges 514 are drawn between the neighboring electrograms, i and j. Edges 514 enforce the local activation time difference constraint, $\Delta$. Graph 500 utilizes a difference constrain, $\Delta=2$, i.e., a local activation time for a given electrogram, i, should be within one sample of a local activation time for a neighboring electrogram, j.

Edges 512 are drawn between samples of electrogram i and between samples of electrogram j. Edges 512 are assigned a weight equal to the energy, w, for that sample of electrogram i or electrogram j. For example, edge 512 drawn between sample t and t+1 for electrogram i has a weight of $w_i(t)$.

According to embodiments of the systems and methods described herein, the energy, $w_i$, or response of a given electrogram i, may be computed using one of several computation methods, including, for example, and without limitation, a wavelet-based response computation based on the surface ECG. In alternate embodiments, the surface ECG traces are summed to generate a single representative ECG trace that is used for QRS blanking. For example, for a surface ECG producing twelve traces, each discretized into 15 samples within a given WOI, the response for the surface ECG is computed according to EQ. 3 and EQ. 4, below, which illustrate the dv/dt method:

$$r(t) = \sum_{i=1}^{12} r_i(t) \qquad \text{EQ. 3}$$

$$r_i(t) = \left|\frac{dv}{dt}\right| \qquad \text{EQ. 4}$$

where, $$\left|\frac{dv}{dt}\right|$$

is the absolute value of the first time derivative of the ECG signal, i.e., a change in voltage over a change in time of the ECG, or slope. The response, r(t), is then normalized, i.e., inverted, to a range of [0,1], to get the energy, w(t).

Similarly, in certain embodiments, the response of an electrogram, i, is computed using the dv/dt method. Processor 114 computes an energy, $w_i(t)$, for a given electrogram, i, using the energy for the surface ECG described above in EQ. 3 and EQ. 4, referred to now as $w_{surf}(t)$. For a bipole electrogram discretized into 10 samples within the WOI:

$$w_i(t) = \alpha(\max(r_i(t)) - r_i(t)) + \beta \cdot w_{surf}(t) \qquad \text{EQ. 5}$$

where, $r_i(t)$ is defined in EQ. 4, and $\alpha$ and $\beta$ are constants. The energy, $w_i(t)$, is then normalized to a range of [0,1]. For a unipole electrogram discretized into 10 samples within the WOI:

$$w_i(t) = \alpha(\max(r_i(t)) - r_i(t)) + \beta \cdot w_{surf}(t) \qquad \text{EQ. 6}$$

where, $r_i(t)$ is defined by EQ. 7, below, and with $w_i(t)$ is normalized to a range of [0,1].

$$r_i(t) = -\frac{dv}{dt} \qquad \text{EQ. 7}$$

where, $$\frac{dv}{dt},$$

is the first time derivative of the electrogram signal, i.e., a change in voltage over a change in time of the electrogram, or slope.

Figure 3:
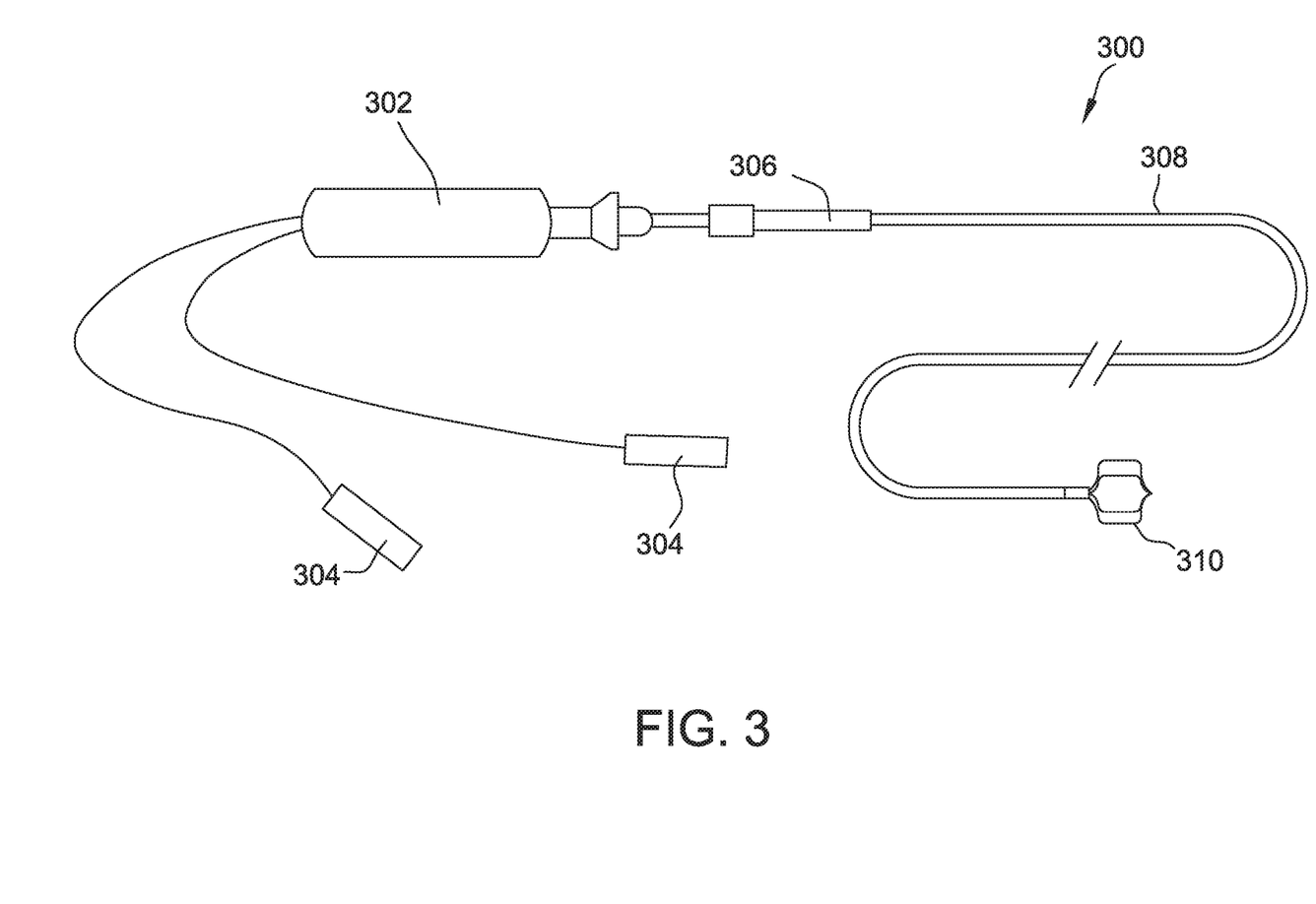
FIG. 3A is a schematic diagram of an exemplary catheter system for use in the system shown in FIG. 1 and FIG. 2.
FIG. 3B is a schematic diagram of an exemplary electrode assembly for use in the catheter system shown in FIG. 3A.
Figure 6:
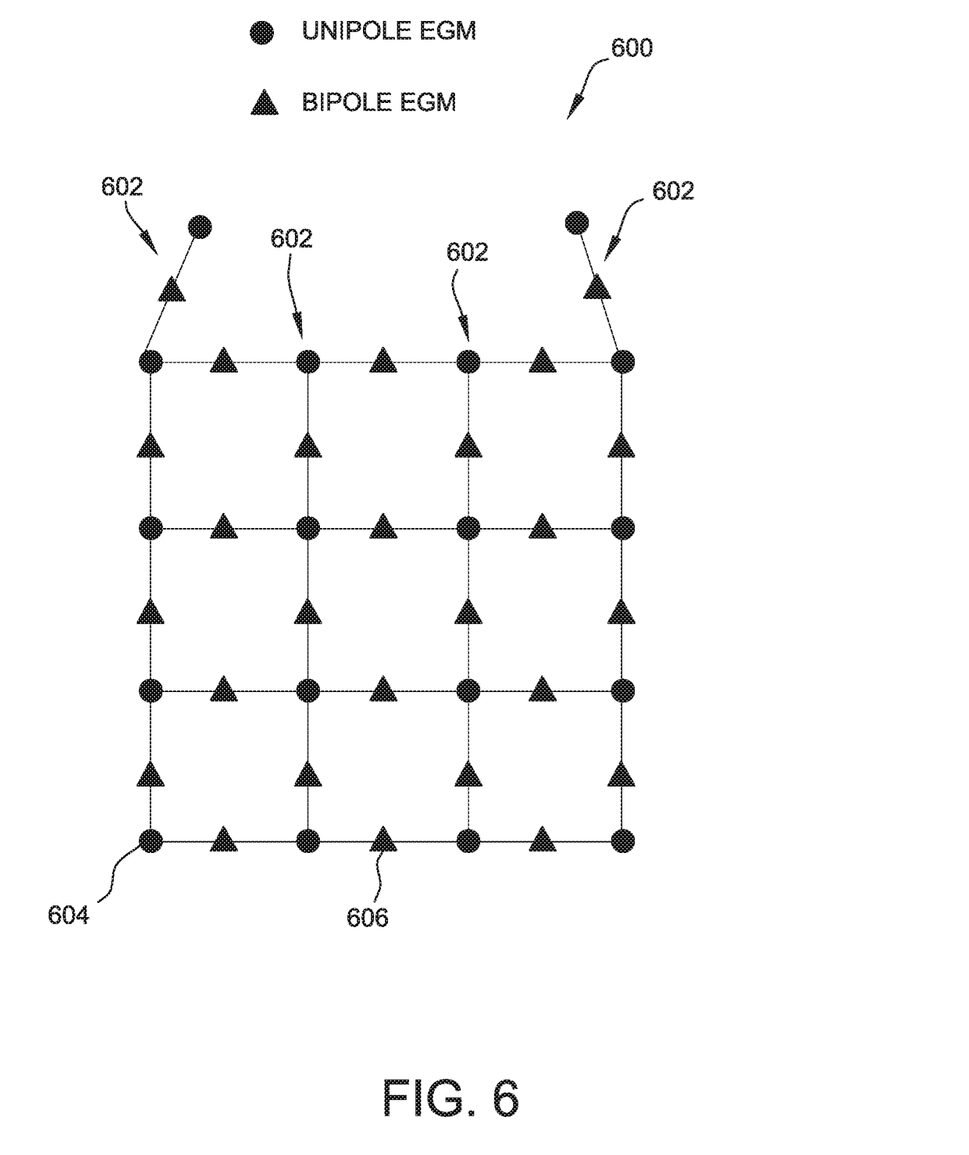
FIG. 6 is an illustration of an exemplary neighborhood of electrograms.

FIG. 6 is an illustration of an exemplary neighborhood 600 of electrograms corresponding to a basket catheter, such as, for example, catheter 120 shown in FIG. 3, having 18 total electrodes 604 on four splines 602. The 18 electrodes are arranged such that the first spline 602 has five electrodes 604, the second and third splines 602 have four electrodes 604, and the fourth spline has five electrodes 604. In the illustration of FIG. 6, electrodes 604 are unipole electrodes represented by circles. Each neighboring pair of unipole electrodes forms a bipole electrode 606, represented by triangles. For a given bipole or unipole electrode, its neighborhood is defined by its connecting edges. The neighborhood illustrated in FIG. 6 is applicable to any catheter having a planar configuration of electrodes, and that maintains its inter-electrode spatial distance when deployed in the cardiac chamber.

Figure 7:
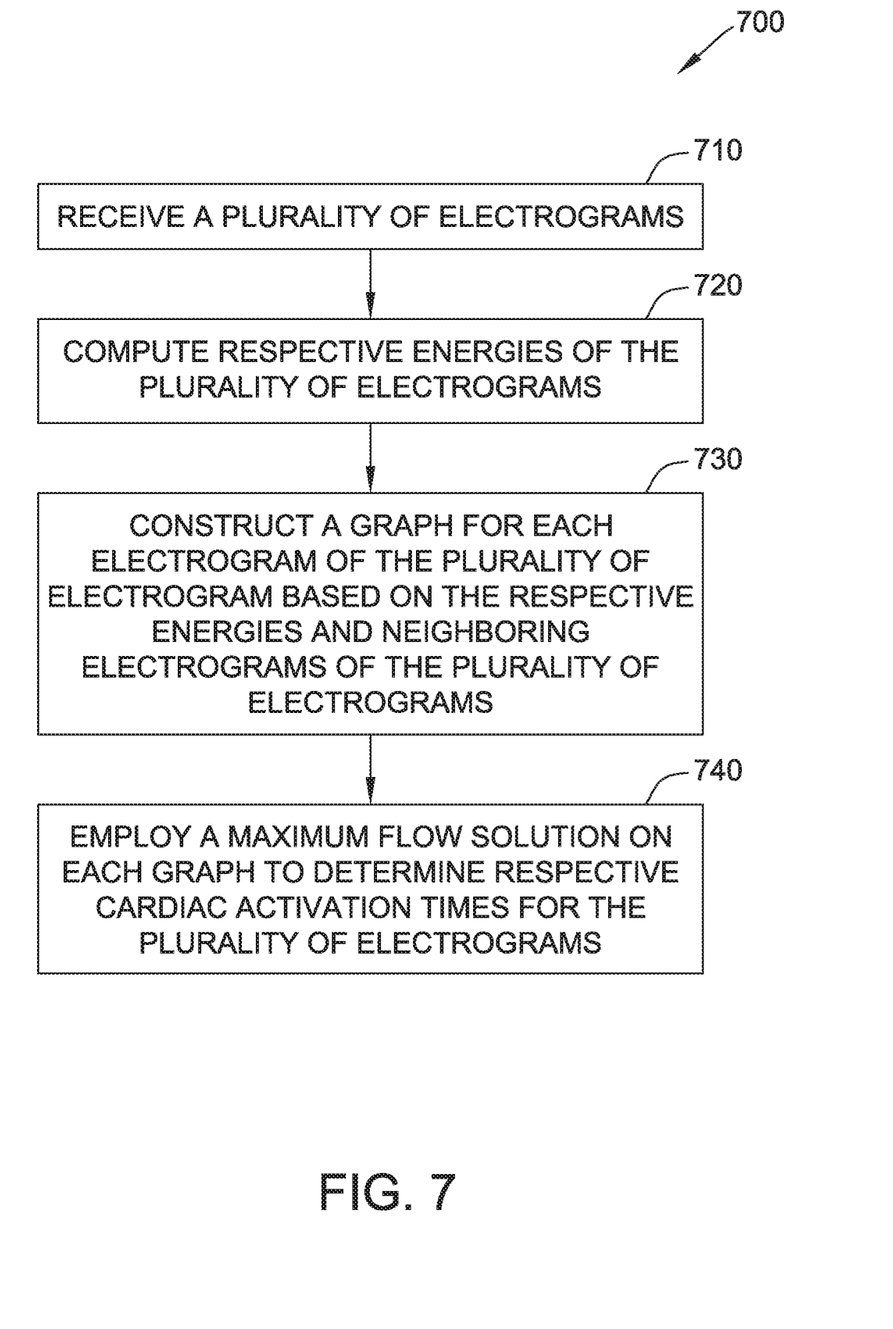
FIG. 7 is a flow diagram of an exemplary method of detecting cardiac activation times.

FIG. 7 is a flow diagram of an exemplary method 700 of detecting cardiac activation times for a patient 102's heart 122. A plurality of electrograms are detected at DAQ 110 and received 710 at computing system 112 for further processing by processor 114. Processor 114 computes 720 respective energies, w, of the plurality of electrograms. The energies are based on computed activation responses, i.e., responses, r, for each of the electrograms using one of several possible computation methods, such as the wavelet method and the dv/dt method.

Processor 114 constructs 730 a graph, such as, for example, graph 500 shown in FIG. 5, for each of the electrograms based on the respective energies and neighboring electrograms of the plurality of electrograms. Graph 500 includes one node for each sample of electrogram i and electrogram j, which are indexed by t. Graph 500 also includes edges 510, 512, and 514. Graph 500 is arranged to form a maximum flow problem.

Processor 114 employs 740 a maximum flow solution, as described above with respect to FIG. 5, to determine respective cardiac activation times for the plurality of electrograms.

In certain embodiments of method 700, for mapping irregular cardiac rhythms, once a first solution is found by employing 740 the maximum flow solution, a refractory parameter is set and graph 500 is split into the left and right portions, or sub-electrograms, with respect to the "minimum cut." The maximum flow method is then recursively applied to the reconstructed sub-graphs of graph 500 from the remaining nodes, such that another cardiac activation time is detected. As described above with respect to EQs. 3-7, each of the electrograms, for the purpose of generating data for the sub-graphs of graph 500, may need further discretization to produce additional samples for computation of the respective energies.

Figure 8:
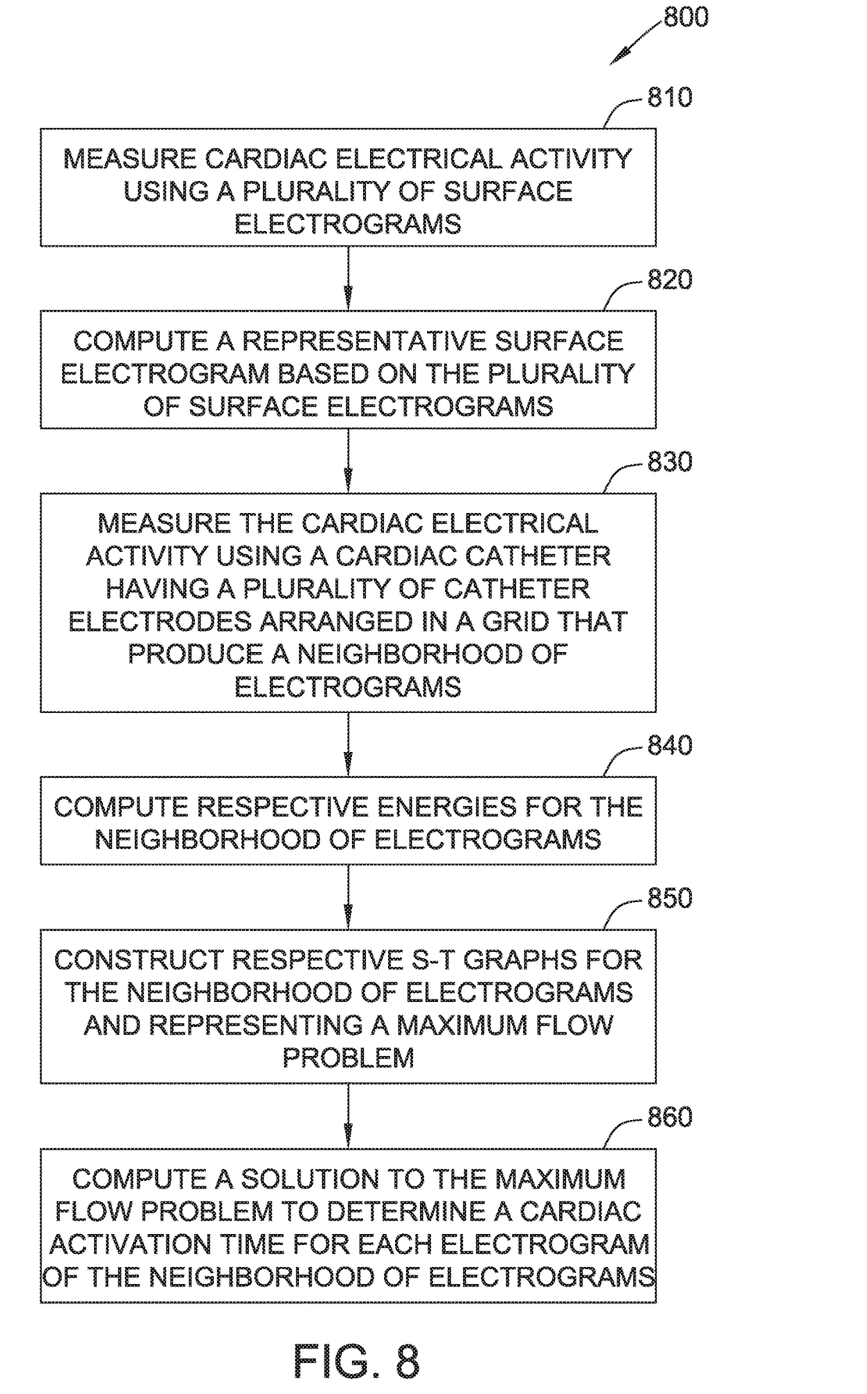
FIG. 8 is a flow diagram of an exemplary method of conducting an ECG on a patient.

FIG. 8 is a flow diagram of an exemplary method 800 of conducting an ECG on patient 102. Cardiac electrical activity within patient 102 is measured 810 using a plurality of surface electrograms generated by limb electrodes 104 and precordial electrodes 106, which include both bipole and unipole electrodes, and detected by DAQ 110. A representative surface electrogram is computed 820 from the plurality of surface electrograms by computing system 112 and, more specifically, processor 114. The representative surface electrogram may be computed, for example, according to EQ. 3 and EQ. 4.

The cardiac electrical activity is further measured 830 using cardiac catheter 120, such as catheter system 300 shown in FIG. 3, having a plurality of catheter electrodes arranged on a basket 310 or other configuration, such as, for example neighborhood 600. Processor 114 computes 840 respective energies for the neighborhood 600 of electrograms. The energies may be computed, for example, according to EQ. 5 and EQ. 6.

Processor 114 constructs 850 an s-t graph, such as, for example, graph 500, for the neighborhood 600 of electrograms. The constructed graph 500 represents a maximum flow problem. Processor 114 computes 860 a solution to the maximum flow problem to determine a cardiac activation time for each electrogram of neighborhood 600 of electrograms.

The technical effects of the embodiments described above may include: (a) providing an interactive user interface for viewing cardiac activation detections from bipole and unipole electrograms side-by-side; (b) providing a visualization of depolarization waves in a given radius, or neighborhood of a selected electrogram; (c) improving cardiac activation detection for a WOI in which multiple cardiac activations occur; (d) detecting cardiac activation times for unipole and bipole electrograms simultaneously; (e) utilizing a neighborhood of electrograms to detect cardiac activations in a given electrogram; (f) optimizing cardiac activation detections for a given set of electrograms; and (g) providing QRS blanking based on surface ECG.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A system for detecting cardiac activation times of a patient, the system comprising:
a data acquisition system configured to detect a plurality of electrograms generated at a plurality of respective electrodes coupled to the patient; and
a processor communicatively coupled to the data acquisition system and configured to:
receive the plurality of electrograms from the data acquisition system,
compute respective energies of the plurality of electrograms, and
detect a cardiac activation time for a first electrogram among the plurality of electrograms based on the respective energy of the first electrogram and the respective energy of a second electrogram that neighbors the first electrogram.

2. The system of claim 1, wherein the plurality of electrograms comprises a surface electrocardiogram.

3. The system of claim 2, wherein the processor is further configured to sum respective responses of the surface electrocardiogram into a single representative electrocardiogram.

4. The system of claim 3, wherein the processor is further configured to compute the respective energies of the plurality of electrograms based on the single representative electrocardiogram of the surface electrocardiogram.

5. The system of claim 1 further comprising a display on which the cardiac activation time detected for the first electrogram is presented to a user.

6. The system of claim 1, wherein the processor is further configured to:
compute respective discretized energies for the plurality of electrograms;
construct a graph for each pair of neighboring electrograms among the plurality of electrograms, the graph representing the respective discretized energies and a local activation time difference constraint enforced on each pair of neighboring electrograms.

7. The system of claim 1, wherein the data acquisition system comprises a plurality of analog and digital circuits for interfacing a surface electrocardiogram and at least one cardiac catheter comprising a plurality of electrodes.

8. A method of detecting cardiac activation times for a patient's heart, said method comprising:
receiving a plurality of electrograms;
computing respective energies of the plurality of electrograms;
constructing a graph for representing the plurality of electrograms based on the respective energies and respective neighboring electrograms of the plurality of electrograms; and
employing a maximum flow solution on each graph to determine respective cardiac activation times for the plurality of electrograms.

9. The method of claim 8, wherein computing an energy, of the respective energies, for an electrogram, i, comprises computing an inverse of a response for the electrogram, wherein the response for the electrogram is equal to an absolute value of a slope of the electrogram at a time t when the electrogram corresponds to a bipole electrode, and wherein the response for the electrogram is equal to a negative of the slope of the electrogram at time t when the electrogram corresponds to a unipole electrode.

10. The method of claim 8, wherein receiving a plurality of electrograms comprises receiving a plurality of surface electrograms.

11. The method of claim 10, wherein computing an energy, of the respective energies, for an electrogram, i, comprises computing the energy according to the formula: $\alpha(\max(r_i(t))-r_i(t))+\beta \cdot w_{surf}(t)$, wherein $\alpha$ and $\beta$ are predetermined constants, $r_i(t)$ is a computed response for the electrogram, and $w_{surf}(t)$ is a representative energy based on a sum of respective responses of the plurality of surface electrograms.

12. The method of claim 8, wherein receiving a plurality of electrograms comprises receiving at least one bipole electrogram.

13. The method of claim 8, wherein receiving a plurality of electrograms comprises receiving at least one unipole electrogram.

14. The method of claim 8, wherein constructing the graph for an electrogram, i, and a neighboring electrogram, j, comprises defining a node for each sample of a plurality of discrete samples of the plurality of electrograms.

15. The method of claim 14, wherein constructing the graph for the electrogram, i, and the neighboring electrogram, j, further comprises:
defining a first plurality of edges representing the respective energies at each sample of the plurality of discrete samples; and
defining a second plurality of edges representing a local activation time difference constraint between the electrogram i and the neighboring electrogram j.

16. The method of claim 8 further comprising:
selecting a refractory parameter;
constructing left and right subgraphs for at least one electrogram of the plurality of electrograms; and
employing a maximum flow solution on the left and right subgraphs to detect at least one additional cardiac activation time for the at least one electrogram.

17. The method of claim 8 further comprising computing a local activation time (LAT) map of the heart.

18. A method of conducting an electrocardiogram (ECG) on a patient, said method comprising:
measuring cardiac electrical activity using a plurality of surface electrograms;
computing a representative surface electrogram based on the plurality of surface electrograms;
measuring the cardiac electrical activity using a cardiac catheter having a plurality of catheter electrodes arranged in a grid that produce a neighborhood of electrograms;
computing respective energies for the neighborhood of electrograms;
constructing an s-t graph for the neighborhood of electrograms and representing a maximum flow problem; and
computing a solution to the maximum flow problem to determine a cardiac activation time for each electrogram of the neighborhood of electrograms.

19. The method of claim 18 wherein constructing the s-t graph, for each electrogram, i, of the neighborhood of electrograms, comprises:
defining a source node, s, and a sink node, t;
defining a first plurality of nodes representing each discrete sample of the electrogram;
defining a second plurality of nodes representing each discrete sample of a neighboring electrogram, j;
defining a first plurality of edges among the first plurality of nodes and among the second plurality of nodes, the first plurality of edges representing the respective energies of electrogram i and electrogram j; and
defining a second plurality of edges between the first plurality of nodes and the second plurality of nodes, the second plurality of edges representing a local activation time difference constraint on the cardiac activation times determined for electrogram i and electrogram j.

20. The method of claim 19, wherein computing the solution to the maximum flow problem comprises determining a minimum cut that severs the source node from the sink node and minimizes the total energy of detected cardiac activation times for the plurality of electrograms.

* * * * *